US00PP31916P2

(12) United States Plant Patent
McGuckin et al.

(10) Patent No.: US PP31,916 P2
(45) Date of Patent: Jun. 30, 2020

(54) ***SETCREASEA* PLANT NAMED 'EDGE OF NIGHT'**

(50) Latin Name: *Setcreasea pallida*
Varietal Denomination: Edge of Night

(71) Applicants: Donna Jayne McGuckin, O'Fallon, MO (US); Thomas Patrick McGuckin, Jr., O'Fallon, MO (US)

(72) Inventors: Donna Jayne McGuckin, O'Fallon, MO (US); Thomas Patrick McGuckin, Jr., O'Fallon, MO (US)

( * ) Notice: Subject to any disclaimer, the term of this patent is extended or adjusted under 35 U.S.C. 154(b) by 0 days.

(21) Appl. No.: 16/602,390

(22) Filed: Sep. 26, 2019

(51) Int. Cl.
*A01H 5/02* (2018.01)
*A01H 6/00* (2018.01)

(52) U.S. Cl.
USPC ..... Plt./257
CPC ..... *A01H 6/00* (2018.05)

(58) Field of Classification Search
USPC ..... Plt./257
CPC ..... A01H 5/02
See application file for complete search history.

*Primary Examiner* — Kent L Bell
(74) *Attorney, Agent, or Firm* — Penny J. Aguirre

(57) ABSTRACT

A new hybrid cultivar of *Setcreasea* plant named 'Edge of Night' that is characterized by its leaves that are pale green in color with dark purple veins on lower surfaces, its leaves that are dark purple in color with a distinct leaf margin that is bright green in color on the upper surfaces, its foliage coloration that is consistent on all leaves with no reversion observed, and its flowers that are pink in color.

2 Drawing Sheets

Genus and species: *Setcreasea pallida.*
Variety denomination: 'Edge of Night'.

BACKGROUND OF THE INVENTION

The present invention relates to a new and distinct plant of *Setcreasea pallida*, hereinafter referred to by its cultivar name, 'Edge of Night'. 'Edge of Night' represents a new wandering jew or purple heart; a tender perennial that is grown as a houseplant or as an annual for use in containers and hanging baskets in all climates.

The Inventors discovered the new cultivar in summer of 2016 as a naturally occurring chimeral mutation of unnamed and unpatented plant of *Setcreasea pallida* that was growing in a container block in his nursery in Wentzville, Mo.

Asexual propagation of the new cultivar was first accomplished by one of the Inventors by stem cuttings in July of 2016 in Wentzville, Mo. Asexual propagation by stem cuttings has determined that the characteristics of the new cultivar are stable and reproduced true to type in successive generations.

SUMMARY OF THE INVENTION

The following traits have been repeatedly observed and represent the characteristics of the new cultivar. These attributes in combination distinguish 'Edge of Night' as a new and unique cultivar of *Setcreasea.*

1. 'Edge of Night' exhibits leaves that are pale green in color with dark purple veins on the lower surfaces.
2. 'Edge of Night' exhibits leaves that are dark purple in color with a distinct leaf margin that is bright green in color on the upper surfaces.
3. 'Edge of Night' exhibits foliage coloration that is consistent on all leaves with no reversion observed.
4. 'Edge of Night' exhibits flowers that are pink in color.

The parent of 'Edge of Night' is similar to 'Edge of Night' in having upper leaf surfaces that are dark purple in color but differs from 'Edge of Night' in having upper leaf surfaces that lack a bright green margin, lower leaf surfaces that are dark purple in color and flowers that are darker pink in color. 'Edge of Night' can be most closely compared to the *Setcreasea* cultivar 'Pink Corazon' (also known as 'Pink Stripes', 'Variegata' and 'Tri Color' (not patented)). 'Pink Corazon' differs from 'Edge of Night' in having foliage that is variegated with stripes of purple, green, and pink with the variegation being highly variable or even lacking (solid purple), in lacking light green lower leaf surfaces and bright green margins, and in having purple flowers.

BRIEF DESCRIPTION OF THE DRAWINGS

The accompanying colored photographs illustrate the overall appearance and distinct characteristics of the new *Setcreasea*, 'Edge of Night'. The photographs were taken of a plant two months in age of the new cultivar as grown in a 22-cm container (from 5 cuttings) in a greenhouse in Wentzville, Mo.

The photograph in FIG. 1 provides an overall view of the plant habit and foliage coloration of plant of 'Edge of Night'.

Figure 1:
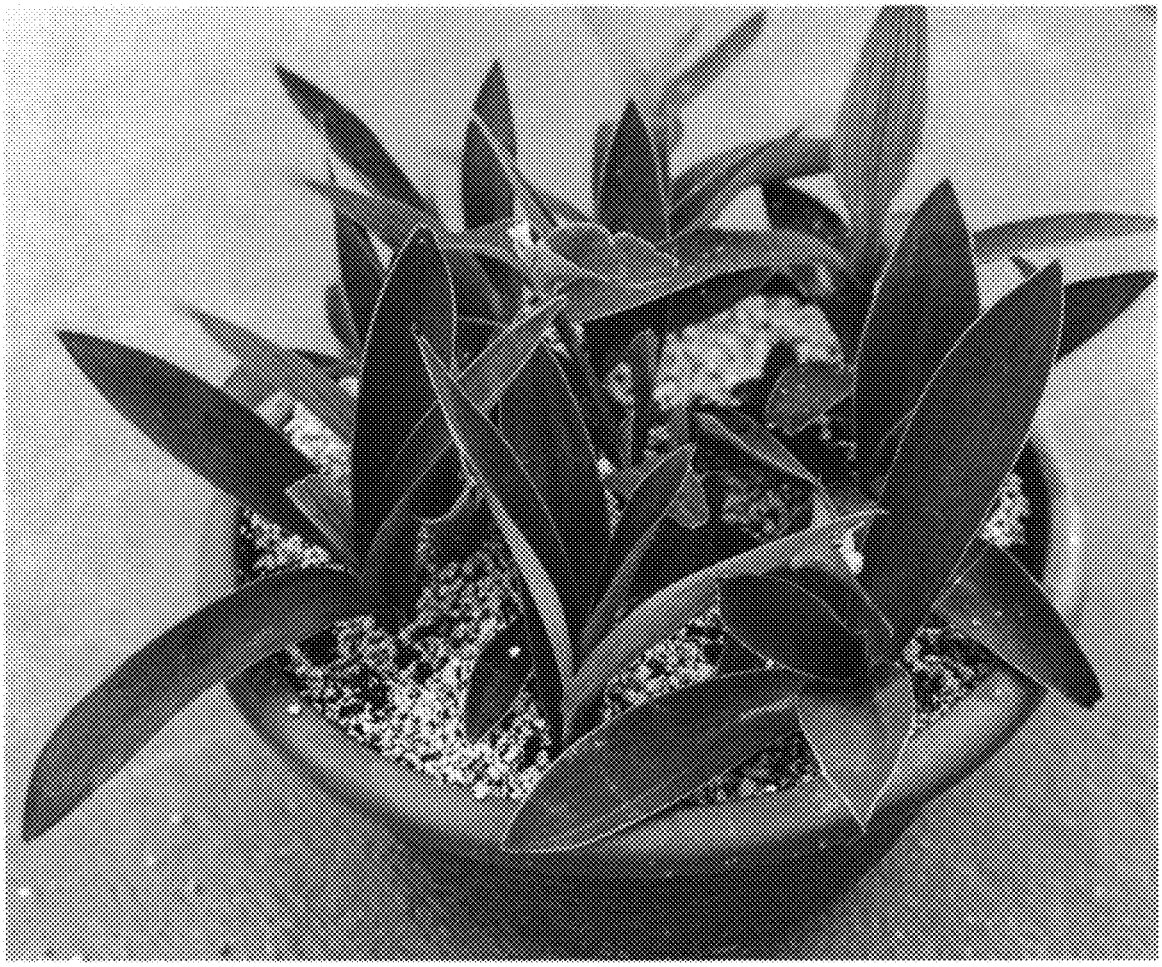
Figure 2:
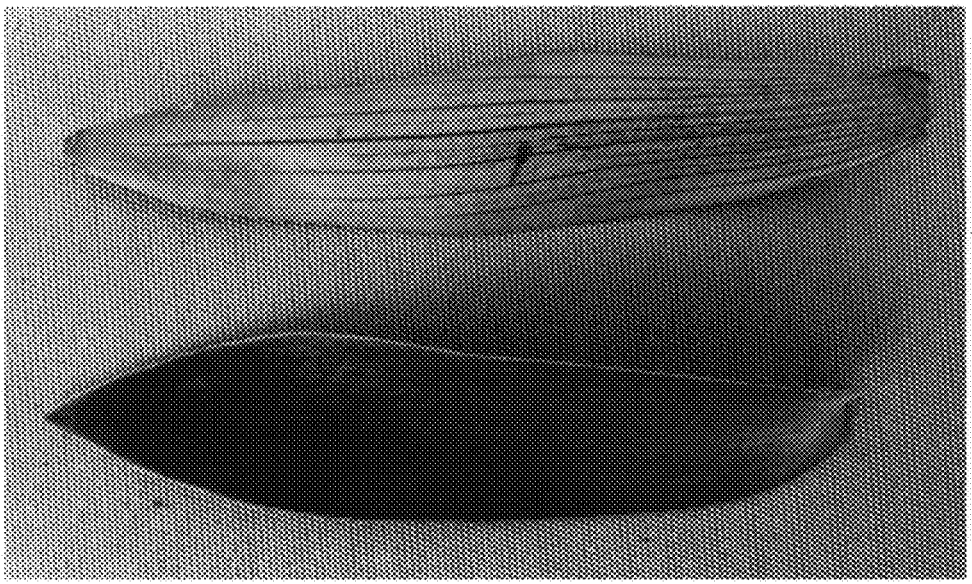

The photograph in FIG. 2 provides a close-up view of an upper (on top) and lower leaf (on bottom) of 'Edge of Night'.

Figure 3:
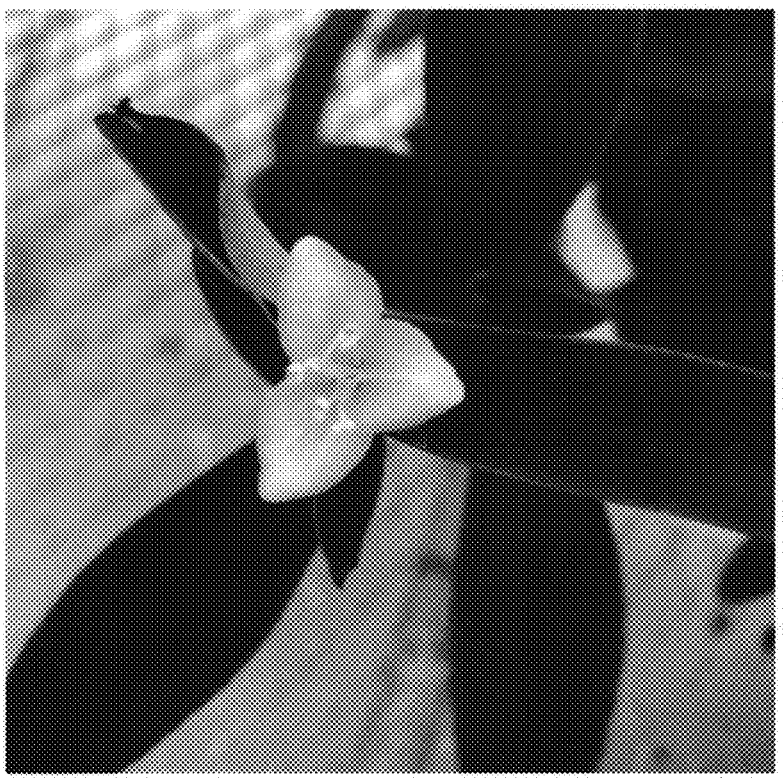

The photograph of FIG. 3 provides a close-up view of a flower of 'Edge of Night'.

The colors in the photographs are as close as possible with the photographic and printing technology utilized and the color values cited in the Detailed Botanical Description accurately describe the colors of the new *Setcreasea.*

BOTANICAL DESCRIPTION OF THE PLANT

The following is a detailed description of two-month-old plants of the new cultivar as grown in a 22-cm container (from 5 cuttings) in a greenhouse in Wentzville, Mo. The phenotype of the new cultivar may vary with variations in environmental, climatic, and cultural conditions, as it has not been tested under all possible environmental conditions. The color determination is in accordance with The 2007 Colour Chart of The Royal Horticultural Society, London, England, except where general color terms of ordinary dictionary significance are used.

General description:

*Blooming period*.—Sporadically throughout the year in Wentzville, Mo.

*Plant type*.—Evergreen tender perennial; grown as an annual or house plant in all climates.

*Plant habit*.—Spreading and cascading.

*Height and spread*.—An average of 30 cm in height and 60 cm spread as grown in a 22-cm container (from 5 cuttings) as a two-month-old plant.

*Cold hardiness*.—At least to U.S.D.A. Zones 7 to 10.

*Diseases and pests*.—No susceptibility or resistance to diseases or pests has been observed.

*Root description*.—Fleshy long roots 162C in color with fibrous side roots 162C in color.

*Propagation*.—Stem cuttings.

*Root development*.—Average of 2 weeks for root initiation and an average of 4 weeks to produce a young plant in a 4-container (dependent on growing temperatures).

*Growth rate*.—Vigorous.

Stem description:

*Shape*.—Round, slightly oval.

*Stem color*.—Young and mature stems (unsheathed); N77A with fine stripes of 191A.

*Stem size*.—Average of 6 mm in diameter up to 18 cm in length when blooms emerge.

*Stem surface*.—Glabrous.

*Branching*.—Basal branches, no lateral branches.

*Stem number*.—Average of 14, with 1 to 2 offshoots formed at base.

*Internode length*.—Average of 3 cm between leaf blades.

Foliage description:

*Leaf shape*.—Lanceolate.

*Leaf division*.—Simple.

*Leaf base*.—Clasping and sheathed around stem.

*Leaf apex*.—Narrowly acute.

*Leaf venation*.—Parallel, typically 4 pairs of veins surrounding midrib, color on upper and lower surface 79A.

*Leaf margins*.—Entire, very slightly undulated.

*Leaf attachment*.—Clasping, no petiole.

*Leaf arrangement*.—Alternate.

*Leaf aspect*.—Held at an average angle of 30° to horizontal (vertical 0), slightly concave.

*Leaf substance*.—Strong and leathery.

*Leaf surface*.—Upper and lower surfaces glabrous with margins on basal portion of margins pubescent with fine long hairs; average of 2 mm in length and too fine to measure color.

*Leaf color*.—Newly formed leaves and mature leaves upper surface; N137A and 138A towards base and heavily suffused with 79A and margin 1 mm in width 144A, lower surface; 191A with sparse speckling of 79A between veins, leaf sheath (inner and outer surface); 191A with veins N79C and slightly suffused with N79C between veins.

*Leaf size*.—Leaf blade; up to 13 cm in length and 3.6 cm in width, sheath; an average of 2.2 cm in length and 5 mm in width.

*Leaf quantity*.—Average of 10 per stem 18 cm in length.

Flower description:

*Inflorescence type*.—Terminal umbel-like cyme, bloom sequentially with only one bloom open at a time.

*Lastingness of inflorescence*.—Individual blooms last about one day, inflorescence blooms for about 4 weeks.

*Inflorescence size*.—Average of 2 cm in width and 2.5 cm in depth with 1 flower open.

*Flower fragrance*.—None.

*Bracts*.—2 per inflorescence, 1 larger; an average of 5.8 cm in length and 1.8 cm in width, lanceolate in shape, 1 smaller; an average of 3.6 cm in length and 2.2 cm in width, ovate in shape, all other characteristics similar to leaves.

*Flower buds*.—Oval in shape, average of 17 mm in length and 4 mm in width, color is 137D and 139D (sepal portion) and 71A in color (petal portion), pubescent surface.

*Flower type*.—Open bell-shaped.

*Flower aspect*.—Held upward to terminus.

*Flower size*.—About 2.4 cm in depth, about 2 cm in width.

*Flower number*.—Average of 8 per inflorescence.

*Petals*.—3, spatulate in shape, acute apex, entire margin, attenuate base, average of 1.5 cm in length and 8 mm in width, glabrous on upper and lower surface, a blend of 75B and 76B in color slightly blending with 155B at apex on both surfaces, thin in substance.

*Sepals*.—3, 1.2 cm in length, 2 mm in width, lanceolate in shape, narrowly acute apex, entire margin, lower 1/3 fused at base, held upright, color on inner and outer surface; a blend of 155A and 144D, outer surface slightly shiny appearance and covered with long white hairs 3 mm in length and NN155D in color, inner surface glabrous and glossy.

*Peduncles*.—None, sessile to stem.

*Pedicels*.—Average of 7 mm in length and 2.2 mm in width, 155B in color, covered with long wooly white hairs 3 mm in length and 155C in color.

Reproductive organs:

*Gynoecium*.—Pistil; 1, style is 1.1 cm in length and 0.7 mm in width and 76D in color, stigma is club shaped, 0.7 mm in diameter and 11D in color, ovary is 1.5 mm in length and width, globose-oblong in shape, and 145D in color.

*Androecium*.—6 stamens, anther is basifixed, oval in shape with flattened apex, 1 mm in length and 1.5 mm in width, 15A in color, filament is 1.5 cm in length and 76C in color, glabrous and shiny surface, pollen is moderate in quantity and 7A in color.

*Fruit and seeds*.—Not observed.

It is claimed:

1. A new and distinct cultivar of *Setcreasea* plant named 'Edge of Night' substantially as herein illustrated and described.

* * * * *